United States Patent
Verdonck et al.

(10) Patent No.: US 6,668,083 B1
(45) Date of Patent: Dec. 23, 2003

(54) DERIVING GEOMETRICAL DATA OF A STRUCTURE FROM AN IMAGE

(75) Inventors: Bert L. A. Verdonck, Eindhoven (NL); Sherif Makram-Ebeid, Dampierre (FR); Sylvain Devillers, Paris (FR); Philippe Lacour, Le Perreux sur Marne (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/555,870

(22) PCT Filed: Oct. 7, 1999

(86) PCT No.: PCT/EP99/07806

§ 371 (c)(1),
(2), (4) Date: Jun. 7, 2000

(87) PCT Pub. No.: WO00/22572

PCT Pub. Date: Apr. 20, 2000

(30) Foreign Application Priority Data

Oct. 9, 1998 (EP) .............................. 98402509

(51) Int. Cl.$^7$ ................................. G06K 9/46
(52) U.S. Cl. ................. 382/203; 382/128; 382/287; 382/311; 382/201
(58) Field of Search ................. 382/103, 128, 382/132, 153–154, 173, 199, 201, 203, 204, 215, 242, 243, 266, 269, 287, 311; 345/418, 419, 420; 348/26, 169

(56) References Cited

U.S. PATENT DOCUMENTS

| | | | | |
|---|---|---|---|---|
| 5,559,901 A | * | 9/1996 | Lobregt ...................... | 382/256 |
| 5,568,384 A | * | 10/1996 | Robb et al. ................. | 715/532 |
| 5,570,430 A | * | 10/1996 | Sheehan et al. ............ | 382/128 |
| 5,751,296 A | * | 5/1998 | Furusawa et al. ........... | 345/520 |
| 5,795,296 A | * | 8/1998 | Pathak et al. ............... | 600/443 |
| 6,130,964 A | * | 10/2000 | Marques et al. ............ | 382/236 |
| 6,259,802 B1 | * | 7/2001 | Jolly et al. .................. | 382/103 |

OTHER PUBLICATIONS

Geiger, et al. "Dynamic programming for detecting, tracking, and matching deformable contours", IEEE, pp. 294–302, 1995.*
Li, et al "A boundary optimization algorithm for delineating brain objects from CT–scans", IEEE,pp. 1553–1557, 1994.*
Guttman, et al. "Tag and contour detection in tagged MR images of the left ventricle", IEEE, pp. 74–88, 1994.*
Williams, et al "A fast algorithm for active contours", IEEE, pp. 592–595, 1990.*
Cohen, et al. "Global minimun for active contour models: a minimal path approach", IEEE, pp. 666–673, 1996.*
"Digital Radiography Segmentation of Scoliotic Vertebral Body Using Deformable Models" by Claude Kauffmann and Jacques A. de Guise in SPIE vol. 3034, 1997, 243–251.

* cited by examiner

Primary Examiner—Daniel Mariam
(74) Attorney, Agent, or Firm—John Vodopia

(57) ABSTRACT

A method of deriving geometrical data of a structure from an image of the structure comprises the selection of marker points in the image. A typical contour is associated with the marker points and the geometrical data is calculated from the typical contour. According to the invention, correctness values are associated with the marker points. The correctness values indicate the reliability of the correspondence of the marker points to typical (anatomical) features in the structure. Furthermore, a cost function is associated with a typical contour, which cost function is dependent on the correctness values of the marker points. The typical contour is arranged in such a manner that the cost function reaches an optimum value, such as a local maximum or minimum value. The method is particularly suitable for deriving geometrical data, such as angles and distances concerning the spinal column of a patient. Preferably, some clearly recognizable marker points are manually indicated and derived marker points are obtained by interpolation between the manually indicated marker points.

9 Claims, 2 Drawing Sheets

DERIVING GEOMETRICAL DATA OF A STRUCTURE FROM AN IMAGE

FIELD OF THE INVENTION

The invention relates to a method of deriving geometrical data of a structure from an image of the structure, in which
marker points are selected in the image,
a typical contour is associated with the marker points, and geometrical data is calculated from the typical contour.

The invention also relates to a data processor which is arranged to carry out such a method.

BACKGROUND INFORMATION

A method of this kind is known from the article *"Digital radiography segmentation of scoliotic vertebral body using deformable models"*, published in SPIE Vol. 3034, 1997.

The known method is intended notably for deriving the degree of deformation, relative to a healthy spinal column, from an image of a spinal column of a patient to be examined. According to the known method, every vertebra is approximately by a deformed standard template. The templates are slightly rounded trapezia having dimensions which correspond to statistically mean dimensions of the respective vertebrae. Such a statistical mean value is determined from the dimensions of the vertebrae of a large number of patients having a spinal column deformed by scoliosis. The respective standard templates are deformed by scaling the height and the individual parallel sides in order to make them correspond as well as possible to the relevant vertebrae in the image. The standard templates are characterized by their height and a number of scale variables. The dimensions of the sides of the standard templates and the radius of curvature of concave sides of the standard templates are respective products of the height and one of the scale variables. Separate values of the height and the scale variables exist for different vertebrae. The known method thus takes into account the fact that the spinal column comprises vertebrae having different shapes and dimensions. The values of the scale variables have been estimated on the basis of data known from literature. The values for the heights have been derived from a large number of X-ray images of scoliotic patients. The typical contour corresponding to the edge of the spinal column in the image is derived from the standard templates. Furthermore, specific positions are indicated on the derived typical contour. A three-dimensional reconstruction of the imaged spinal column is carried out on the basis of said specific positions.

In order to carry out the known method it is necessary to determine characteristic dimensions of a large number of vertebrae in spinal columns of a large number of patients so as to form the standard templates. In order to make the standard templates correspond to the vertebrae in the image, the central axis of the spinal column is estimated by looking and a number of marker points is indicated on the estimated central axis. The central axis is subsequently approximated by a cubic curve through the indicated marker points on the central axis. Subsequently, the standard templates are deformed in such a manner that they are distributed as well as possible along the cubic curve. This makes the known method rather cumbersome. Because the known method utilizes standard templates relating to an average spinal column suffering from scoliosis, the known method is not very well suitable for accurately deriving spatial geometrical data relating to a spinal column exhibiting serious anomalies.

Notably when the image concerns an X-ray image of the spinal column it often occurs that a part of the marker points is not visible. The contrast of the vertebrae reproduced in an X-ray image often is not sufficient to see the marker points. Even if all marker points are visible in the X-ray image, usually not all of them are visible clearly enough to enable accurate indication of their position in the image.

OBJECTS AND SUMMARY OF THE INVENTION

It is an object of the invention to provide a method of deriving geometrical data of a structure from an image of the relevant structure which is less cumbersome than the known method and, moreover, enables more accurate results to be obtained.

This object is achieved by means of a method of deriving geometrical data of a structure from an image of the relevant structure according to the invention which is characterized in that
correctness values are associated with the marker points,
a cost function is associated with the typical contour,
which cost function is dependent on the shape of the typical contour and on the values of the correctness values, and
which typical contour is chosen in such a manner that the cost function has an optimum value.

For each of the selected marker points the correctness values represent the likelihood that the selected marker point accurately corresponds to a typical anatomical detail of the structure. The use of the method according to the invention notably concerns the determination of spatial geometrical data of the spinal column of a patient to be examined. In this application the marker points are selected to be situated at the positions in the image which correspond to the corner points of the vertebrae and to anatomically typical points at the edges of the relevant vertebral body. It appears that the marker points are not always suitably visibly reproduced in the image; this occurs notably when the image is an X-ray image of the spinal column. It is to be noted, however, that the marker points are not always clearly visible either in, for example magnetic resonance images of the spinal column. By associating the typical contour with the marker points the method according to the invention takes into account that the fact that not all marker points correspond equally accurately to the relevant positions in the spinal column. Upon association of the typical contour the value of the cost function is calculated and the typical contour is determined in such a manner that the cost function has an optimum value. The cost function is dependent on the correctness values of the marker points. It is thus achieved that the typical contour for which the cost function is optimized is determined predominantly by marker points having a high correctness value, i.e. by marker points for which it is rather certain that they accurately correspond to their relevant anatomically typical positions in the structure, such as the spinal column. The typical contour accurately corresponds with the boundary of the structure at issue in the image. Often, such a typical contour is a closed loop, e.g. when the structure is a vertebra. The typical contour may also comprise separate disconnected curves or straight line portions. For example, the correctness value of individual marker points is dependent on the differences between the brightness value in the marker point and brightness values in positions in the image in the vicinity of the relevant marker point. Generally speaking, suitable marker points correspond to anatomically typical positions; in that case differences between the brightness value in the relevant marker point and in individual directions adjacent the relevant marker point have values which are more or less predetermined. For example, such differences occur when the marker point is situated at the corner of a bone, such as a vertebra, which is surrounded by softer and less dense tissue, such as muscular tissue or lung tissue. The better the correspondence between such differences in the image and the predetermined differences, the higher the likelihood of accurate correspondence between the relevant marker point and the corresponding typical anatomical position. Therefore, the correctness values are preferably dependent on the predetermined differences or gradients in separate directions of brightness values in the vicinity of the relevant marker point. Marker points for which it is uncertain whether they correspond to their relevant anatomical position have a comparatively small effect only on the typical contour. Because the cost function is also dependent on the shape of the typical contour, it is achieved that the association of a typical contour having improbable shapes is counteracted and that, conversely, the association of a typical contour having expected, frequently occurring shapes is favored. For example, the cost function is chosen in such a manner that a high value of the cost function is associated with typical contours where the direction of the typical contour abruptly changes in many locations.

In the context of the method according to the invention the optimum value of the cost function is to be understood to mean the value of the cost function associated with a typical contour which accurately represents the geometry of the relevant structure. This means that the typical contour is formed in such a manner that for a curve which is associated with the marker points but deviates from the typical contour, the value of the cost function is, for example higher or lower than the optimum value; the optimum value is in that case a (local) maximum or a (local) minimum, respectively.

Using the method according to the invention it is achieved that the typical contour accurately represents the spatial geometry of the structure, notably the spinal column of the patient to be examined. The typical contour is, for example a curve through the centers of the successive vertebrae. The typical contour may also represent the edge of the spinal column. The course in space of the spinal column of the patient to be examined can be derived from the variation of the typical contour. This course in space is represented notably by the values of a small number of so-called Cobb angles and the mutual orientations of the individual vertebral bodies. The Cobb angles are the angles enclosed by the upper side and the lower side of respective vertebrae relative to one another. The Cobb angles of individual pairs of vertebrae offer an accurate indication of the three-dimensional shape of the spinal column. It has been found notably that the method according to the invention is a suitable technical aid for accurately following the development of deformations, as caused by scoliosis, of the spinal column of the patient to be examined. The invention is also suitable for deriving the geometrical data of the rib cage of the patient to be examined.

These and other aspects of the invention will be elaborated on the basis of the following embodiments which are defined in the dependent claims.

Preferably, according to the invention first a number of marker points is indicated by hand. Among all relevant marker points there are usually a number which are clearly visible in the image. Such clearly visible marker points can be readily indicated by hand. Such indications can be realized, for example by displaying the image on a monitor of a workstation and by indicating the marker points by means of a cursor, the position of the cursor upon indication of the respective marker points being stored. The marker points can also be indicated by touching them on the display screen of the monitor by means of a pointer and by storing the positions of the points where the display screen is touched by the pointer. The marker points can also be indicated by indicating these points on a radiological film by means of a digitizer. It has been found that in many situations the positions of marker points which are not or only poorly visible in the image can be derived from the indicated marker points. It is notably when the structure whereto the image relates has been determined in advance that it is usually possible to derive from indicated marker points other marker points which are situated therebetween. To this end, it is merely necessary to indicate the most clearly visible marker points and the user need not make the effort of searching poorly visible marker points in the image. It is notably when the image concerns a periodic structure that the derived marker points can be found very well on the basis of the indicated marker points. The positions of the derived marker points can be simply found by interpolation between the positions of the indicated marker points. It is notably when the image concerns a periodic structure that very accurate results are obtained by way of interpolation.

The imaged structure may be of a rather complex spatial shape; the imaged structure may notably comprise a plurality of sectors. Some of these sectors are suitably visible in the image whereas other sectors are much more difficult to distinguish. In such a situation it is handy to indicate the indicated marker points only in the indicated sectors. The derived marker points in the derived sectors can be derived from the indicated marker points in the indicated sectors. The derived sectors may be, for example difficult to distinguish in the image. Because the number of sectors and, for example, also the periodicity of the succession of sectors of the structure are usually known, indicated and derived marker points can be readily determined in all indicated and derived sectors. Overlooking of sectors can be easily avoided by ensuring that the derived marker points are chosen in such a manner that, in conjunction with the indicated marker points, they represent the already known number of sectors with the correct periodicity. It is also possible to save time by manually indicating the indicated marker points in only a small number of indicated sectors. If the image concerns a spinal column, the sectors relate to individual vertebrae.

The typical contour preferably represents the central axis of the structure. It is notably when the image structure has an elongate shape that the central axis indicates predominantly the spatial orientations of individual parts of the structure relative to one another. It is particularly advantageous to take the central axis of the spinal column of the patient to be examined as the typical contour. The central axis then accurately indicates the orientations of the individual (groups of) vertebrae relative to one another. It has been found that the central axis of the spinal column can be accurately derived by plotting a smooth curve, such as a poly-Bezier curve, a cubic curve or a spline curve, through a small number of derived marker points. Such derived marker points are preferably taken for successive vertebrae, each time halfway between two marker points at oppositely situated corner points of one and the same vertebra.

Another typical contour represents an edge of the imaged structure. This typical contour may comprise a plurality of parts, each of which represents a separate edge of the imaged structure. The typical contour representing such an edge of the structure can be accurately determined, inter alia on the basis of gradients or differences between brightness values in the image. The differences between brightness values to both sides of such an edge is usually much larger than those within or outside the imaged structure. The typical contour representing an edge of the imaged structure may also relate to the edges of individual sectors. Such a typical contour representing an edge in the image is preferably derived from a gradient image of the image. Such a gradient image contains differences between brightness values in neighboring positions in the image of the structure. The gradient image preferably also contains the direction of the brightness gradients in the image. This means that the gradient image associates the vector (magnitude and direction) of the brightness gradient with different positions in the image. The cost function of the typical contour is chosen in such a manner that curves along which large brightness gradients occur in the gradient image, for example in a predetermined direction, are strongly favored in the image.

In many cases the approximate angle enclosed by an edge of a sector relative to the central axis of the structure is known in advance. For example, edges of individual vertebrae extend transversely of the central axis of the spinal column. In order to facilitate the search for the edges of the individual sectors, use is made of a cost function which associates optimum values with typical contours along positions having large brightness gradients in the direction which corresponds to the already known angle relative to the central axis. A suitable cost function is, for example dependent on the scalar product of the brightness gradient and the directional vector along the typical contour.

These and other aspects of the invention will be described in detail hereinafter on the basis of the following embodiments and with reference to the accompanying drawing which illustrates the invention on the basis of an example concerning the imaging of the spinal column of the patient to be examined; therein:

DETAILED DESCRIPTION OF THE INVENTION

In the present example the images are X-ray images of a spinal column of the patient to be examined. Each X-ray image shows a shadow projection of the spinal column. The invention, however, can be used equally well for other types of images, for example a computer tomography image, a magnetic resonance image or an ultrasound image.

Figure 1:
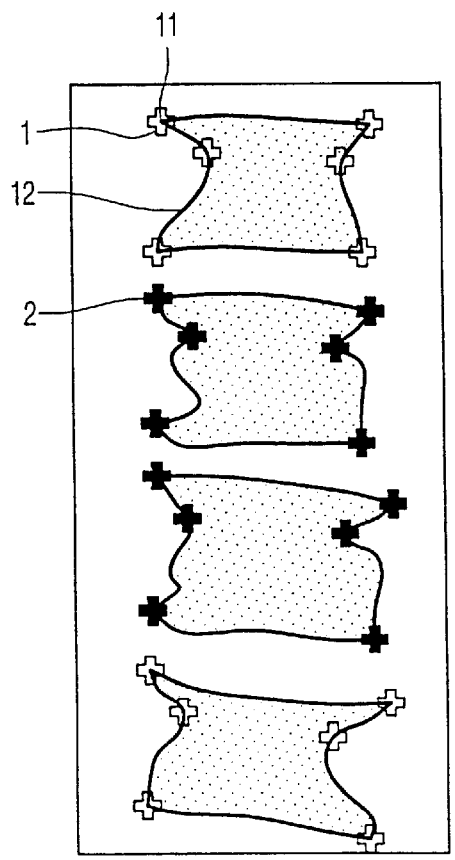
FIG. 1 illustrates the manual indication of the indicated marker points and the derivation of the derived marker points.

FIG. 1 illustrates the manual indication of the indicated marker points and the derivation of the derived marker points. FIG. 1 notably shows an X-ray image of the spinal column of the patient to be examined. The manually indicated marker points are represented by the white crosses 1. The white crosses have been made at clearly recognizable corner points 11 and at two clearly recognizable points on the inner edge 12 of the vertebrae by the user. Positions of the derived marker points 2 are calculated on the basis of the positions of the indicated marker points and on the basis of the known number of vertebrae present between the vertebrae on which the indicated marker points are indicated. The derived marker points 2 are represented by black crosses in FIG. 1. A first estimate of the positions of the derived marker points 2 is made by interpolation of positions of the indicated marker points 1. The calculation of the derived marker points 2 is refined by calculating the exact positions of the derived marker points 2 in the estimated positions of the derived marker points 2 on the basis of the brightness gradients in different directions.

Figure 2:
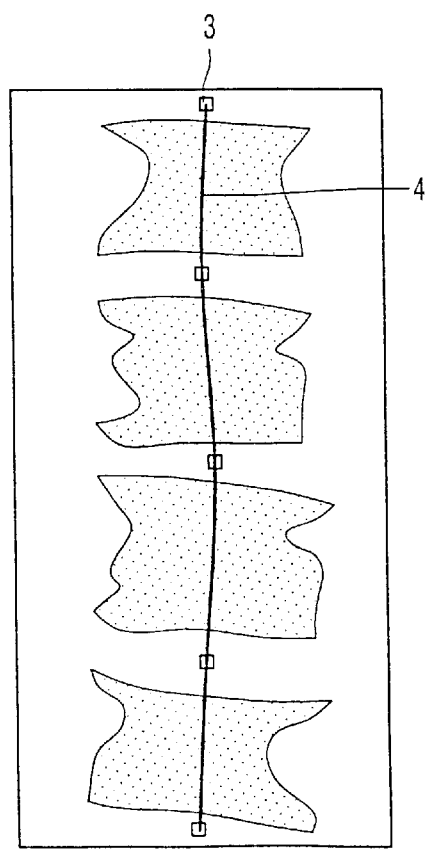
FIG. 2 shows a typical contour which represents the central axis of the structure.

FIG. 2 shows a typical contour which represents the central axis of the structure. This typical contour is calculated by first determining center points 3, each of which is situated halfway between two oppositely situated marker points 1, 2 as shown in FIG. 1. The center points 3 themselves are also derived marker points which relate to the respective anatomical centers of the relevant vertebrae. Subsequently, preferably a poly-Bezier curve is plotted through the center points 3. This poly-Bezier curve is the typical contour 4 representing the central axis of the spinal column. It is to be noted, however, that it is equally well possible to derive the typical contour 4 representing the central axis by associating a curve with the center points by way of a least error method. In the case it is not necessary for the typical contour 4 to pass through all center points 3. In the course of the derivation of the typical contour 4 as a poly-Bezier curve or the use of the least error method, it is advantageous to take into account the correctness values at the center points, so that the typical contour 4 is influenced mainly by center points having high correctness values.

Figure 3:
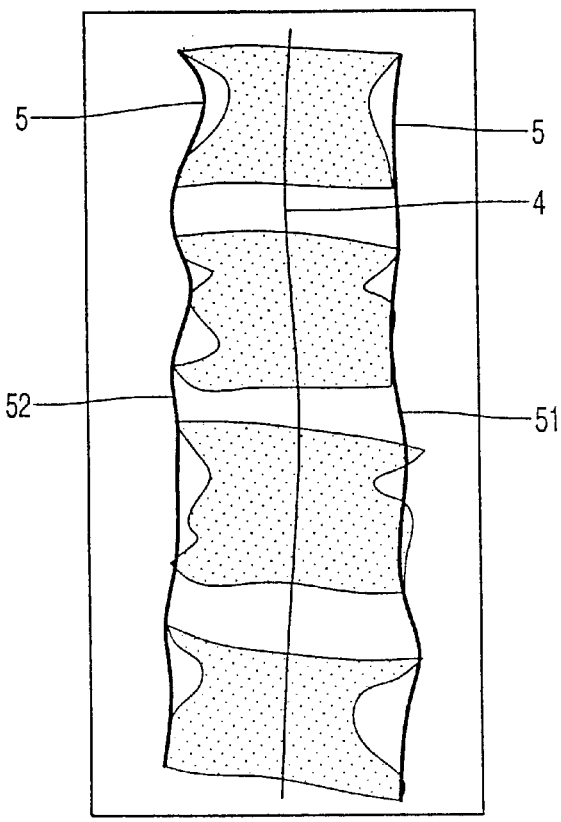
FIG. 3 shows a typical contour which represents the edges of the structure.

FIG. 3 shows a typical contour 5 which represents the edges of the structure. The typical contour 5 is notably multi-coherent, because the typical contour comprises two separate sub-curves 51, 52. Each of the sub-curves 51, 52 denotes an edge of the structure, i.e. of the spinal column. The two sub-curves are derived on the basis of the typical contour representing the central axis by checking, for lines extending approximately parallel to the central axis, where in the image strong brightness gradients occur in a direction transversely of the central axis.

Figure 4:
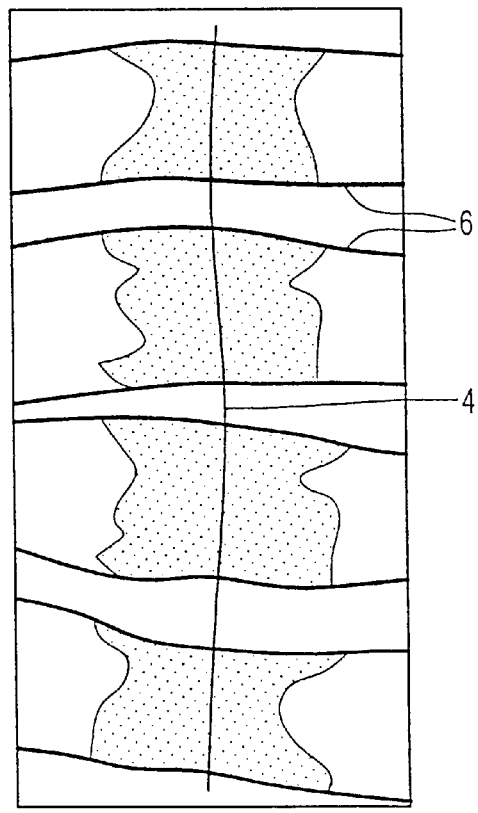
FIG. 4 shows typical contours which represent sector boundaries in the structure.

FIG. 4 shows typical contours 6 which represent sector boundaries in the structure. The structure shown is a spinal column with a plurality of vertebrae; in the present example the individual vertebrae constitute the sectors of the structure. The individual boundaries are derived by checking, starting from a large number of points on the typical contour 4 representing the central axis and along lines transversely of the typical contour, where in the image large brightness gradients occur in a direction approximately parallel to the central axis. This operation is performed by determining an optimum path in the image on the basis of the cost function, the value of the cost function for these lines being larger as the brightness gradients along these lines are larger in the direction parallel to the central axis. Furthermore, the cost function is selected in such a manner that pairs of lines which are situated at a distance from one another which corresponds to the mean height of the vertebrae are further favored.

The values for a set of geometrical parameters which are representative of a deformation, if any, of the spinal column are calculated from the various typical contours. Examples of such geometrical parameters are the Cobb angles, the heights of the vertebrae and the distances between vertebrae. The values of these geometrical parameters for the relevant patient to be examined can be derived from the typical contours by means of simple calculations. It is also possible to calculate a three-dimensional reconstruction of the spinal column from the combination of various typical contours. It that case it is advantageous to derive individual typical contours from a plurality of images. Such a plurality of images may reproduce, for example projection shadow images from different projection directions.

The method according to the invention yields a set of geometrical data which a physician can use as a technical aid in making a diagnosis, for example as regards the degree of scoliosis.

The method according to the invention is preferably carried out by means of a data processor as defined in claim 10. A data processor of this kind is, for example a computer or an electronic (micro)processor which is programmed to carry out the various functions of the data processor according to the invention. The data processor may also be constructed as a special purpose processor comprising electronic circuits which are specifically arranged to execute the various functions of the data processor according to the invention.

What is claimed is:

1. A method of deriving geometrical data of a structure from a single image of the structure, comprising the steps of:

selecting marker points in the single image;

determining derived marker points in the single image from the selected marker points;

associating a typical contour with the derived marker points;

calculating geometrical data from the typical contour;

associating correctness values with the derived marker points;

associating a cost function with the typical contour;

wherein the cost function is dependent on the shape of the typical contour and on the values of the correctness values;

wherein the typical contour is chosen in such a manner that the cost function has an optimum value and the selecting of the marker points comprises a manual indication of marker points.

2. The method as defined by claim 1, wherein the derived marker points are derived from the manually indicated marker points by interpolation.

3. The method as defined by claim 1, wherein the typical contour represents a central axis of the structure.

4. The method as defined by claim 1, wherein the typical contour represents an edge of the structure.

5. The method as defined by claim 4, further comprising the steps of:

calculating a gradient image from the image, and deriving the typical contour from the gradient image.

6. The method as defined by claim 1, wherein the structure comprises a plurality of sectors, the marker points are manually indicated in a number of indicated sectors, the derived marker points are determined in derived sectors, and the derived sectors are situated between indicated sectors.

7. The method as defined by claim 6, wherein the typical contour comprises sector boundaries of one or more sectors.

8. The method as defined by claim 1, further comprising the steps of:

associating a central typical contour which represents a central axis of the structure with the marker points;

associating an edge contour which represents an edge of the structure with the marker points;

deriving the direction of the edge typical contour on the basis of the direction of the central typical contour; and deriving the direction of the central typical contour on the basis of the direction of the edge typical contour.

9. A data processor which derives geometrical data of a structure from a single image, selects derived marker points in the single image, determines derived marker points in the single image from the selected marker points, associates a typical contour with the derived marker points in the single image, calculates the geometrical data from the typical contour, associates correctness values with the marker points, associates a cost function with the typical contour, which cost function is dependent on the shape of the typical contour and on the values of the correctness values, selects the typical contour in such a manner that the value of the cost function is optimum and wherein the selection of the marker points comprises a manual indication of marker points.

* * * * *